(12) United States Patent
McCormac

(10) Patent No.: US 7,635,772 B2
(45) Date of Patent: Dec. 22, 2009

(54) PROCESS FOR THE PREPARATION OF OLIGONUCLEOTIDES

(75) Inventor: Paul McCormac, Grangemouth (GB)

(73) Assignee: Avecia Biotechnology Inc., Milford, MA (US)

( * ) Notice: Subject to any disclaimer, the term of this patent is extended or adjusted under 35 U.S.C. 154(b) by 427 days.

(21) Appl. No.: 10/539,625

(22) PCT Filed: Dec. 16, 2003

(86) PCT No.: PCT/GB03/05464

§ 371 (c)(1),
(2), (4) Date: Jan. 3, 2006

(87) PCT Pub. No.: WO2004/055036

PCT Pub. Date: Jul. 1, 2004

(65) Prior Publication Data

US 2006/0149052 A1    Jul. 6, 2006

(30) Foreign Application Priority Data

Dec. 18, 2002 (GB) ................. 0229443.7
Apr. 25, 2003 (GB) .................... PCT/GB03/01795

(51) Int. Cl.
C07H 21/02 (2006.01)
C07H 21/04 (2006.01)
C07D 275/06 (2006.01)

(52) U.S. Cl. .............. 536/25.31; 536/25.33; 536/25.34; 548/210; 548/211

(58) Field of Classification Search ................. 424/486; 536/25.4
See application file for complete search history.

(56) References Cited

U.S. PATENT DOCUMENTS

| 6,140,493 | A | 10/2000 | Dower et al. | |
| 6,274,725 | B1 * | 8/2001 | Sanghvi et al. | 536/25.34 |
| 7,247,720 | B2 * | 7/2007 | Sinha | 536/25.33 |
| 7,501,505 | B2 * | 3/2009 | Sinha et al. | 536/25.34 |
| 2006/0041114 | A1 * | 2/2006 | Sinha et al. | 536/24.3 |

FOREIGN PATENT DOCUMENTS

| WO | 00/02953 | 1/2000 |
| WO | 02/46205 | 6/2002 |
| WO | 03/004512 | 1/2003 |
| WO | WO03/004512 | * 1/2003 |
| WO | 03/091267 | 11/2003 |

OTHER PUBLICATIONS

Eleuteri et. al. Organic Process Research & Development, 2000, 4 182-189.*
Adams et al., "A Reinvestigation of the Preparation, Properties, and Applications of Aminomethyl and 4-Methylbenzhydrylamine Polystyrene Resins" Journal of Organic Chemistry (1998) vol. 63, pp. 3706-3716.*
Moriguchi et al., "Synthesis and Properties of Aminoacylamido-AMP: Chemical Optimization for the Construction of an N-Acyl Phosphoramidate Linkage" Journal of Organic Chemistry (2000) vol. 65 p. 8229-8238.*
Bardella et al., "Polystyrene-Supported Synthesis by the Phosphite Triester Approach: An Alternative for the Large scale Synthesis of Small Oligodeoxyribonucleotides", Tetrahedron Letters, 31(43):6231-6234 (1990).
Wright et al., "Large Scale Synthesis of Oligonucleotides via Phosphoramidite Nucleosides and a High-loaded Polystyrene Support", Tetrahedron Letters, 34(21):3373-3376 (1993).
Xavier et al., "Criteria for the Economic Large Scale Solid-Phase Synthesis of Oligonucleotides", Tetrahedron, 50(8):2617-2622 (1994).

* cited by examiner

Primary Examiner—Shaojia Anna Jiang
Assistant Examiner—Eric S Olson
(74) Attorney, Agent, or Firm—Morgan Lewis Bockius LLP

(57) ABSTRACT

A process for the synthesis of an oligonucleotide is provided in which an oligonucleotide is assembled on a swellable solid support using the phosphoramidite approach in the presence of an activator, wherein the activator is not tetrazole or a substituted tetrazole. Preferred activators are pyridinium, imidazolinium and benzimidazolinium salts; benzotriazole and derivatives thereof; and saccharin or a saccharin derivative. Preferred swellable solid supports comprise functionalised polystyrene, partially hydrolysed polyvinylacetate or poly(acrylamide).

11 Claims, No Drawings

PROCESS FOR THE PREPARATION OF OLIGONUCLEOTIDES

This application is a 371 of PCT/GB03/05464, filed Dec. 16, 2003 and claiming priority benefit under 35 U.S.C. § 119 (a)-(d) and 365(c) to United Kingdom application 0229443.7, filed Dec. 18, 2002, and United Kingdom PCT/GB03/01795, filed Apr. 25, 2003.

The present invention concerns a process for the preparation of oligonucleotides.

Oligonucleotides are conventionally prepared by solid phase synthesis wherein the nascent oligonucleotide is coupled to a solid support. Conventionally, phosphoramidite chemistry in the presence of a tetrazole or substituted tetrazole activator is employed to effect the sequential coupling of nucleosides. The solid supports employed in the majority of synthetic applications are rigid, non-swellable supports, particularly controlled pore glass and rigid polystyrene. A number of attempts have been made to employ swellable supports, which offer advantages in terms of much higher potential loadings. These too have employed conventional tetrazole-based activators. Generally, the results have been disappointing, giving either slow coupling reactions or requiring very high amounts of activator.

Surprisingly, it has now been found that the selection of a particular class of activators enables significantly improved synthesis of oligonucleotides using phosphoramidite chemistry and swellable supports.

According to the present invention, there is provided a process for the synthesis of an oligonucleotide in which an oligonucleotide is assembled on a swellable solid support using the phosphoramidite approach in the presence of an activator, wherein the activator is not tetrazole or a substituted tetrazole.

Activators which can be employed in the process of the present invention include salts of heteroaromatic compounds comprising fewer than four nitrogen atoms in the heteroaromatic ring, especially heteroaromatic compounds comprising a 5 or 6 membered ring which comprises one or two nitrogen atoms. Examples include pyridinium, imidazolinium and benzimidazolinium salts, particularly the hexafluorophosphate, tetrafluoroborate, triflate, hydrochloride, trifluoroacetate, dichloroacetate, 0-mesyl, 0-tosyl, bromide or trifluorosulphonyl salts as disclosed in PCT application WO 99/62922 (incorporated herein by reference); benzotriazole and derivatives thereof, especially hydroxybenzotriazole; and saccharin or a saccharin derivative, preferably employed as a salt-complex formed with an organic base, especially the N-methylimidazole, pyridine or 3-methylpyridine salts of saccharin.

Saccharin or saccharin derivatives which can be employed preferably have the general formula:

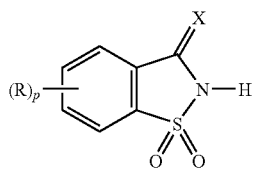

Formula (1)

In Formula 1, p is 0 or an integer from 1 to 4. R for each occurrence is a substituent, preferably each independently, a halo, a substituted or unsubstituted aliphatic group, $-NR^1R^2$, $-OR^3$, $-OC(O)R^3$, $-C(O)OR^3$, cyano, a substituted or unsubstituted aryl, a substituted or unsubstituted heterocyclyl, $-CHO$, $-COR^3$, $-NHCOR^3$, a substituted or unsubstituted aralkyl, halogenated alkyl (e.g., trifluoromethyl and trichloromethyl), or $-SR^3$. Preferably, R is halo, a substituted or unsubstituted aliphatic group, $-NR^1R^2$, $-OR^3$, $-OC(O)R^3$, $-C(O)OR^3$, or cyano. Alternatively, two adjacent R groups taken together with the carbon atoms to which they are attached form a six membered saturated or unsaturated ring. Preferably, the six membered ring formed is an aromatic ring. $R^1$ and $R^2$ are each, independently, $-H$, a substituted or unsubstituted aliphatic group, a substituted or unsubstituted aryl group, a substituted or unsubstituted aralkyl group; or together with the nitrogen to which they are attached form a heterocyclyl group. $R^3$ is a substituted or unsubstituted aliphatic group, a substituted or unsubstituted aryl group, or a substituted or unsubstituted aralkyl group. X is O or S. Preferably, X is O. It is particularly preferred that X is O and p is 0.

Suitable substituents which may be present include aryl groups, halogenated aryl groups, alkyl groups, halogenated alkyl (e.g. trifluoromethyl and trichloromethyl), aliphatic ethers, aromatic ethers, benzyl, substituted benzyl, halogens, particularly chloro and fluoro groups, cyano, nitro, $-S$-(aliphatic or substituted aliphatic group), and $-S$-(aromatic or substituted aromatic) groups.

Preferably the saccharin or saccharin derivative is employed as a salt complex with an organic base.

Organic bases which can form salt-complexes with saccharin or saccharin derivatives are organic compounds that have a tendency to accept protons at pH 7. Preferred organic bases are secondary amines, tertiary amines or azaheterocyclyl bases, each of which may be substituted or unsubstituted by one or more substituents. An aprotic organic base is an organic base that has no hydrogen bonding protons in its chemical structure before accepting a proton. Aprotic organic bases such as tertiary amines and aprotic azaheterocyclyl compounds are preferably used in conjunction with compounds of formula 1, as described herein.

Azaheterocyclyl bases, as used herein, include heteroaryl groups which have one or more nitrogen atom in the aromatic ring and heteroalicyclyl groups that have at least one nitrogen atom in the non-aromatic ring system. Preferably, azaheteroaryl bases have five- or six-membered aromatic rings with from one to three nitrogens in the aromatic ring. Preferably, azaheteroalicyclyl compounds are five- or six-membered rings, commonly comprising one or two nitrogens in the ring. Examples of azaheterocyclyl bases include pyrimidines, 1-alkylpyrazoles, especially 1-($C_{1-4}$ alkyl)pyrazoles, 1-arylpyrazoles, 1-benzylpyrazoles, pyrazines, N-alkylpurines, especially N—($C_{1-4}$ alkyl)purines, N-arylpurines, N-benzylpurines, N-alkylpyrroles, especially N—($C_{1-4}$ alkyl)pyrroles, N-arylpyrroles, N-benzylpyrroles, pyridines, N-alkylimidazoles, especially N—($C_{1-4}$ alkyl)imidazoles, N-arylimidazoles, especially, N-phenylimidazole, N-benzylimidazoles, quinolines, isoquinolines, quinoxalines, quinazolines, N-alkylindoles, especially N—($C_{1-4}$ alkyl)indoles, N-arylindoles, N-benzylindoles, N-alkylbenzimidazoles especially N—($C_{1-4}$ alkyl)benzimidazoles, N-arylbenzimidazoles, N-benzylbenzimidazoles, triazine, thiazole, 1-alkyl-7-azaindoles, especially 1-($C_{1-4}$ alkyl)-7-azaindoles, 1-aryl-7-azaindoles, 1-benzyl-7-azaindoles, pyrrolidines, morpholines, piperidines, and piperazines. Especially preferred azaheterocyclyl bases are pyridines, such as pyridine and 3-methylpyridine, and N—($C_{1-4}$ alkyl) imidazoles, such as N-methylimidazole.

Tertiary amines are organic bases that have a nitrogen atom which is bonded to three carbon atoms, often to three aryl, commonly phenyl, and/or alkyl groups, commonly to three alkyl groups, including for example trialkylamines such as trimethylamine, triethylamine, and diisopropylethylamine. In addition, tertiary amines can be azaheterocyclyl groups wherein the nitrogen atom is aprotic. Tertiary amines that are azaheterocyclyl groups are preferred. Examples of azaheterocyclyl tertiary amines are N-alkylpyrrolidines, N-arylpyrrolidines, N-alkylpyrroles, N-arylpyrroles, N-alkylmorpholines, N-arylmorpholines, N-alkylpiperidines, N-arylpiperidines, N,N-dialkylpiperazines, N,N-diarylpiperazines, N-alkyl-N-aryl-piperazines, quinuclidines, 1,5-diazabicyclo[4.3.0]non-5-enes and 1,8-diazabicyclo[5.4.0]undec-7-enes. Tertiary amines can also be azaheteroaryl or azaheteroalicyclyl compounds.

Secondary amines are organic bases comprising a nitrogen bonded to a single hydrogen and to two carbon atoms. Commonly the nitrogen atom is bonded to two alkyl or aryl groups or forms part of an azaheterocyclic group. Examples of secondary amine compounds include diethylamine and diisopropylamine.

Particularly preferred organic bases include pyridine, 3-methylpyridine, and N-methylimidazole.

Swellable solid supports which can be employed in the process according to the present invention are those which increase in volume when contacted with an appropriate solvent. It will be recognised that the extent of the swelling will vary from support to support, and depending on the nature of the solvent. Preferred swell ratios for a swellable solid support falls in the range of from 5 to 20. The swell ratio is defined as:—

$$\text{Swell Ratio} = \frac{Vol_{final} - Vol_{initial}}{Vol_{initial}}$$

$VOl_{final}$=Final volume occupied by support after allowing the support to fully swell in a given solvent.

$VOl_{initial}$=Initial dry bed volume of support.

Swellable solid supports are typically cross linked polymers wherein the amount of cross-linking is low enough to permit swelling. The extent of crosslinking in these polymers can be expressed in percentage terms and corresponds to the number of moles of polymerisable double bonds derived from monomers containing two or more polymerisable double bonds as a percentage of the total number of moles of polymerisable double bonds. The percentage of cross linking is often in the range of from 0.1, commonly from 0.5, to 20%, such as from 1 to 10%, and preferably no more than 5%. Polymers comprising no more than 20% of cross-linking are generally swellable, whilst polymers comprising greater than 20% of crosslinking are generally not swellable. Most preferably a level of crosslinking from 1% to 5%, especially from 1% to 3% is employed.

The polymer support may be derived from the polymerisation of a composition comprising one or more monomers, and is preferably derived from the polymerisation a composition comprising of two or more monomers. The monomers may contain one or more polymerisable double bonds. Preferably the polymer support is derived from the polymerisation of a composition comprising one or more monomers containing only one polymerisable double bond, and one or more monomers containing two or more polymerisable double bonds. Most preferably the polymer support is derived from the polymerisation of a composition comprising one or two monomers containing only one polymerisable double bond, and one monomer containing two or three polymerisable double bonds.

Examples of monomers containing only one polymerisable double bond include styrene and substituted styrenes such as α-methyl styrene, methyl styrene, t-butyl styrene, bromo styrene and acetoxy styrene; alkyl esters of mono-olefinically unsaturated dicarboxylic acids such as di-n-butyl maleate and di-n-butyl fumarate; vinyl esters of carboxylic acids such as vinyl acetate, vinyl propionate, vinyl laurate and vinyl esters of versatic acid such as VeoVa 9 and VeoVa 10 (VeoVa is a trademark of Shell); acrylamides such as methyl acrylamide and ethyl acrylamide; methacrylamides such as methyl methacrylamide and ethyl methacrylamide; nitrile monomers such as acrylonitrile and methacrylonitrile; and esters of acrylic and methacrylic acid, preferably optionally substituted $C_{1-20}$alkyl and $C_{1-20}$cycloalky esters of acrylic and methacrylic acid, such as methyl acrylate, ethyl acrylate, n-butyl acrylate, 2-ethylhexyl acrylate, i-propyl acrylate, and n-propyl acrylate, methyl methacrylate, ethyl methacrylate, n-butyl methacrylate, 2-ethylhexyl methacrylate, i-propyl methacrylate, n-propyl acrylate, hydroxyethyl acrylate, hydroxyethyl methacrylate, N,N-dimethylaminoethyl acrylate and N,N-dimethylaminoethyl methacrylate. Functional derivatives of the foregoing monomers containing only one polymerisable double bond can also be employed.

Examples of monomers containing two or more polymerisable double bonds include divinylbenzene (DVB), trivinylbenzene, and multifunctional acrylates and methacrylates such as ethylene glycol diacrylate, ethylene glycol dimethacrylate, trimethylolpropane triacrylate, trimethylolpropane trimethacrylate, ethylene bisacrylamide, pentaerythritol triacrylate, pentaerythritol tetraacrylate, pentaerythritol trimethacrylate, pentaerythritol tetramethacrylate and N,N-bis-acryloyl ethylene diamine. Preferably the cross-linking monomer, particularly for the preparation of cross-linked polystyrene, is DVB.

Preferred examples of swellable supports include copolymers comprising polystyrene such as polystyrene-poly(ethylene glycol) copolymers, functionalised polystyrenes, especially polystyrenes funtionalised with polyethylene glycols, including those polymers disclosed in WO00/02953, incorporated herein by reference, polystyrene which is graft-copolymerised with polyethyleneglycol, such as those polymers available under the trade name "Tentagel" which comprise a polystyrene core with polyethylene glycol (MWt ca 4000) chains grafted onto this core, and polymers such as polyvinylacetate. Further preferred supports include partially-hydrolysed poly(vinylacetate). Additionally, poly(acrylamide) supports, especially microporous or soft gel supports, such as those more commonly employed for the solid phase synthesis of peptides may be employed if desired. Preferred poly(acrylamide) supports are amine-functionalised supports, especially those derived from supports prepared by copolymerisation of acryloyl-sarcosine methyl ester, N,N-dimethylacrylamide and bis-acryloylethylenediamine, such as the commercially available (Polymer Laboratories) support sold under the catalogue name PL-DMA. The procedure for preparation of the supports has been described by Atherton, E.; Sheppard, R. C.; in *Solid Phase Synthesis: A Practical Approach*, Publ., IRL Press at Oxford University Press (1984) which is incorporated herein by reference. The functional group on such supports is a methyl ester and this is initially converted to a primary amine functionality by reaction with an alkyl diamine, such as ethylene diamine.

The swellable solid supports comprise a functional group on which oligonucleotide synthesis can be effected. Examples of such functional groups are amino and hydroxy groups.

The oligonucleotide synthesis can take place by direct attachment to the functional group of the solid support. However, in many embodiments, it is preferred to employ a cleavable linker to attach the oligonucleotide to the solid support via the functional group. Examples of such linker are well known in the art and include particularly succinyl, oxaloyl and trityl linkers.

In many embodiments, the support is swelled in the solvent of choice to allow ready access to the functional groups on the support. Solvents of choice can be predicted by considering the polymer composition and are often those solvents which would be "good solvents" for a theoretical linear polymer which may be made from a similar composition but with no crosslinking agent present.

The process of the present invention preferably employs a solvent which is selected to swell the solid support. It will be recognised that the nature of the solvent will be selected based upon the nature of the solid support employed. Examples of suitable solvents suitable for use in phosphoramidite chemistry are well known in the art, and include in particular acetonitrile, dimethylformamide, N-methylpyrrolidinone, dichloromethane, tetrahydrofuran and pyridine.

Oligonucleotides that can be prepared by the process of the present invention include oligodeoxyribonucleotides, oligoribonucleoside, and oligonucleotides comprising mixtures of deoxyribo- and ribonucleosides. The oligonucleotides may be modified by one or more modifications known in the field of oligonucleotide chemistry, for example ribonucleoside moieties may be modified at one or more of the 2'-positions by the presence of 2'-alkoxy group, such as a methoxy or methoxyethoxy group. Deoxyribonucleosides moieties may be modified at the 2'-position by the presence of a substituent, such as a halo group, especially a fluoro group, or by an alkenyl group such as an allyl group. A basic nucleoside moieties may also be present. One or more locked nucleosides may be present. In many embodiments, the oligonucleotides will be in the form of the natural D-isomer. However, some or all of the oligonucleotide may represent an unnatural isomer, for example an L-isomer or a B-anomer, either in whole or in part. The internucleoside linkages may be natural phosphate, or one or more modified linkages, for example phosphorothioate or phosphoramidate linkages may be present.

The oligonucleotide may comprise one or more protecting groups. Examples of such protecting groups, and the positions which they can be employed to protect, are well known to those skilled in the art, and include trityl, monomethoxytrityl and dimethoxytrityl groups, levulinoyl groups, isobutyryl groups, benzoyl groups, acetyl groups and carbonate groups, such as BOC and especially FMOC.

The oligonucleotides may comprise natural and/or unnatural nucleobases including adenine, guanine, cytosine, thymine, uracil, 7-deazaguanine, 7-deaza-8-azaguanine, 5-propynylcytosine, 5-propynyluracil, 7-deazaadenine, 7-deaza-8-azaadenine, 7-deaza-6-oxopurine, 6-oxopurine, 3-deazaadenosine, 2-oxo-5-methylpyrimidine, 2-oxo-4-methylthio-5-methylpyrimidine, 2-thiocarbonyl-4-oxo-5-methylpyrimidine, 4-oxo-5-methylpyrimidine, 2-amino-purine, 5-fluorouracil, 2,6-diaminopurine, 8-aminopurine, 4-triazolo-5-methylthymine, 4-triazolo-5-methyluracil and hypoxanthine.

The oligonucleotide is preferably prepared by coupling a nucleoside phosphoramidite with a nucleoside or oligonucleotide comprising a free hydroxy group, especially by coupling a deoxyribonucleside-3'-phosphoramidite or ribonucleside-3'-phosphoramidite with a nascent oligonucleotide comprising a free 5'-hydroxy group. It will be recognised that the process according to the present invention is equally applicable to the coupling of a 5'-phosphoramidite to a free 3'-hydroxy group.

Preferred phosphoramidites are compounds of formula:

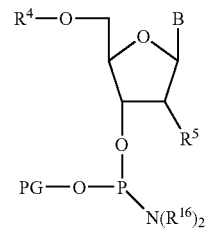

wherein $R^4$ is a protecting group, preferably a trityl, monomethoxytrityl or dimethoxytrityl group, B is a nucleoside base, $R^5$ represents —H, —F —$OR^6$, —$NR^7R^8$, —$SR^9$, or a substituted or unsubstituted aliphatic group, such as methyl or allyl. PG is a phosphorus protecting group, commonly a cleavable phosphorus protecting group employed in oligonucleotide synthesis, and preferably a substituted or unsubstituted aliphatic group or a group of formula —$OCH_2CH_2CN$, —$SCH_2CH_2CN$, —$OR^{11}$, —$SR^{11}$, —O—$CH_2CH_2$—$Si(CH_3)_2C_6H_5$, —O—$CH_2CH_2$—$S(O)_2$—$CH_2CH_3$, —O—$CH_2CH_2$-$C_6H_4$—$NO_2$, —S—$CH_2CH_2$—$Si(CH_3)_2C_6H_5$, —S—$CH_2CH_2$—$S(O)_2$—$CH_2CH_3$, or —S—$CH_2CH_2$—$_{C_6}H_4$—$NO_2$. $R^6$ represents —H, a substituted or unsubstituted aliphatic group (e.g., methyl, ethyl, methoxyethyl or allyl), a substituted or unsubstituted aryl group, a substituted or unsubstituted aralkyl, an alcohol protecting group, especially a base-labile or a silyl protecting group, or —$(CH_2)_q$—$NR^{12}R^{13}$. $R^7$ and $R^8$ are each, independently, —H, a substituted or unsubstituted aliphatic group, or an amine protecting group. Alternatively, $R^7$ and $R^8$ taken together with the nitrogen to which they are attached are a heterocyclyl group. $R^9$ represents —H, a substituted or unsubstituted aliphatic group, or a thiol protecting group. $R^{11}$ represents a substituted or unsubstituted aliphatic group, a substituted or unsubstituted aryl group or a substituted or unsubstituted aralkyl group. $R^{12}$ and $R^{13}$ are each, independently, —H, a substituted or unsubstituted aryl group, a substituted or unsubstituted heteroaryl group, a substituted or unsubstituted aliphatic group, a substituted or unsubstituted aralkyl group, a substituted or unsubstituted heteroaralkyl group or an amine protecting group. Alternatively, $R^{12}$ and $R^{13}$ taken together with the nitrogen to which they are attached form a heterocyclyl group. q is an integer from 1 to about 6. Each $R^{16}$ independently is a $C_{1-6}$ alkyl group, preferably an isopropyl group. The phosphoramidite employed is commonly a betacyanoethyloxy-N,N-diisopropyl phosphoramidite.

The process according to the present invention may employ such process steps as are conventionally carried out for the solid-phase synthesis of oligonucleotides using phosphoramidite chemistry, including sulfurisation, oxidation and capping stages.

When a sulphurization agent is employed, the sulphurization agent may comprise elemental sulfur,. Preferably, the sulfurization agent is an organic sulfurization agent.

Examples of organic sulfurization agents include 3H-benzodithiol-3-one 1,1-dioxide (also called "Beaucage reagent"), dibenzoyl tetrasulfide, phenylacetyl disulfide, N,N,N',N'-tetraethylthiuram disulfide, and 3-amino-[1,2,4]- dithiazole-5-thione (see U.S. Pat. No. 6,096,881, the entire teachings of which are incorporated herein by reference).

Typical reaction conditions for sulfurization of an oligonucleotide using the above agents can be found in Beaucage, et al., *Tetrahedron* (1993), 49:6123, which is incorporated herein by reference.

Preferred sulfurization reagents are 3-amino-[1,2,4]-dithiazole-5-thione and phenylacetyl disulfide.

Sulfurization of an oligonucleotide may be carried out by, for example use of a solution of 3-amino-[1,2,4]-dithiazole-5-thione in an organic solvent, such pyridine/acetonitrile (1:9) mixture or pyridine, having a concentration of about 0.05 M to about 0.2 M.

Examples of oxidising agents which may be employed include iodine and peroxides, such as t-butylhydroperoxide.

A desired oligonucleotide can be prepared for example by a sequence of steps which comprise coupling a protected, commonly a 5'-protected, nucleoside phosphoramidite with a free hydroxy group, oxidising or sulfurising the protected phosphite triester formed in the coupling step to form a phosphate or phosphorothioate oligonucleotide, removing the protecting group from the oligonucleotide, and repeating the cycle until the desired sequence has been assembled. The oligonucleotide can be cleaved from the solid support, and any remaining protecting groups, such as nucleobase and phosphorus protecting groups can be removed using conditions known in the art.

The process according to the present invention can be carried out in a wide range of appropriate reaction vessels, including, for example, columns, stirred vessels and fixed bed reactors.

The present invention is illustrated without limitation by the following example.

EXAMPLE 1

Synthesis of DMTrOABz-3'-Succinate

5'-DMTrOABz-3'-OH (75.0 g, 117 mmol) was charged to an oven-dried 500 ml florentine, followed by succinic anhydride (15.6 g, 160 mmol) and N,N-dimethylaminopyridine. The flask was flushed with nitrogen gas and the neck was fitted with a rubber septum. Anhydrous pyridine (250 ml) was charged to the flask via syringe. The resulting solution was stirred at room temperature for 82 hours after which the bulk of the pyridine was removed in vacuo. The resulting crude oil was stored in a stoppered flask for 50 hours.

The oil was dissolved in dichloromethane (DCM, 250 ml) and this solution was washed with water (2×250 ml) and triethylammonium phosphate solution (3 M, pH 7.5, 250 ml). The organic layer was separated, dried with $MgSO_4$ and the solvent was removed in vacuo. The residue was dissolved in toluene (200 ml) and the solvent was removed in vacuo. This was repeated once more with toluene (200 ml) and once with DCM (200 ml).

This yielded an off-white foam which, after 3 hours drying under vacuum, could be crushed to a free-flowing powder (94.4 g).

The strength of this product was measured (HPLC, area %) as 97%, corresponding to a yield of 91%.

Preparation of 5'-HOABz-3'-succinate-polystyrene Resin

Aminomethylated polystyrene resin (1% crosslinked with divinylbenzene) obtained from Novabiochem (cat. no. 01-64-0010) (5 g, "5.65 mmol", 1 eq) was placed in a large straight-edged sinter funnel and pre-swollen with N-methylpyrrolidinone (NMP, ca. 30 ml), applying a positive pressure of nitrogen via a side-arm to bubble through the thick paste. The NMP was discharged after ca. 10 minutes.

5'-DMTrOABz-3'-succinate (19.4 g, 3.9 eq) and hydroxybenzotriazole (HOBt) (4.6 g, 6 eq) were dissolved in NMP (ca. 35 ml) and diisopropylcarbodiimide (DIC, 2.1 g, 2.9 eq) was added to this solution. Diisopropylethylamine (1.7 g, 3 eq) was added to this solution ca. two minutes after the DIC had been added. This whole solution was swirled then quickly added to the swollen resin in the sinter, again with a positive pressure of nitrogen from below the sinter providing agitation for the thick yellow gel. Glassware and equipment contaminated with DIC was detoxified in a caustic bath.

The sinter funnel was covered over to prevent contamination of the reaction mixture (non-gastight seal) and the reaction was left bubbling gently for 65 hours.

Checking the progress of the reaction by standard Kaiser tests gave a negative result (yellow colour) after this period and the reaction was deemed complete.

The reagent solution was discharged by swapping the $N_2$ flow for a vacuum and sucking the solution into the flask. The resin was washed with NMP (3×~40 ml). Any remaining free amino groups were capped by adding a solution of acetic anhydride (4.2 g, 7.2 eq) and N,N-dimethylaminopyridine (0.07 g, 0.1 eq) in NMP (~35 ml) and holding for 1 hour. The reagents were discharged and the resin was washed with dimethylformamide (DMF, 5×40 ml), DCM, (5×40 ml) and was finally collapsed with diethyl ether (3×40 ml). The resin was blown dry with a stream of nitrogen and dried in a vacuum oven at room temperature overnight. The spent reagent solution was treated with NaOH solution for detoxification.

The resin (1.028 g) was charged to a jacketed phase reactor and washed with DCM (~10 ml). The reactor jacket was cooled to 0° C. with a fluid circulator. While suction was applied, 3% v/v dichloroacetic acid solution in DCM (84 ml) was charged to the reactor. A deep red colour developed Immediately. Once all of the acid solution had passed through the resin bed (110 s) the resin was washed with DMF (5×~10 ml) and DCM (5×~10 ml) and finally collapsed with diethyl ether (3×~20 ml).

Preparation of 5'-AcOG(isobu)TABzCBzABz-3'-polystyrene Resin

For all "dry" steps in coupling reactions (i.e. pre-coupling washes to sulfurization) the DMF used was commercial anhydrous DMF (ex Aldrich), which was dried overnight over molecular sieves in ca. 100 ml batches as required. This gave DMF with a moisture content of 10-50 ppm (Karl-Fischer), c.f. ~150 ppm as initially supplied. Discharging solutions was achieved in these steps by applying a positive pressure of $N_2$ gas to the top of the reactor via the Rotaflo tap. The resin used initially in this series of reactions was 0.5 $mmolg^{-1}$ of the HOABz-polystyrene resin prepared above. All phosphoramidites were protected deoxyribo-3'-betacyanoethyloxy-N,N-diisopropylphosphoramidites.

The HOABz-polystyrene resin (1.356 g, 0.69 mmol) was charged to the jacketed solid-phase reactor, which was fitted with a septum inlet and a Rotaflo tap. Both the nitrogen inlet and outlet were fitted with in-line drying tubes filled with self-indicating $P_2O_5$. The resin was washed with dry DMF (3×~5 ml) and dry DCM (2×~5 ml). The amidite (1.41 g, 2.5 eq) was dried azeotropically with MeCN (2×10 ml) and dissolved in dry DCM (~3 ml). N-methylimidazole salt of saccharin (0.45 g, 2.5 eq) was charged to an oven-dried vial fitted with a septum and dissolved in dry DMF (~0.75 ml) and dry DCM (~1.5 ml). The amidite and saccharin salt solutions were then charged to the pre-swollen resin, in that order.

After a two hour hold with gentle bubbling of the mixture with N$_2$ gas, dry methanol (~2 ml) was added. After ca. 5 minutes the solution was discharged from the reactor and the resin was washed with dry DMF (3×~5 ml) and dry pyridine (2×~5 ml). The spent reagent solution was analysed by HPLC to estimate the amount of active amidite remaining at the end of reaction.

A solution of 3-amino-[1,2,4]-dithiazole-5-thione (0.25 g, 2.5 eq) in dry pyridine (~4 ml) was charged to the resin and this was held, with gentle N$_2$ bubbling, for one hour after which the solution was discharged. The top was removed from the reactor and the resin was washed with bench DMF (5×~5 ml) and DCM (5×~5 ml) and then with Cap A solution (5:3:2 MeCN:Pyridine:N-methylimidazole, 2×~5 ml). Cap A solution (2.5ml) and Cap B solution (4:1 MeCN:Ac$_2$O, 2.5 ml) were then charged to the reactor and the mixture was held for one hour.

The spent capping solution was discharged and the resin was then washed with DMF (5×~5 ml) and DCM (5×~5 ml) and finally with diethyl ether (3×~5 ml). The resin was then left overnight before detritylation.

Prior to detritylation the reactor jacket was cooled to 0° C. and the resin was washed/pre-swollen with DCM. The resin was held under suction while a 3% dichloroacetic acid solution (in DCM) was passed through the bed, causing a deep red colouration to appear. The volume used was based on 100 ml of 3% acid solution per 1 mmol DMT expected to be attached to the resin. Once all the acid solution had passed through the resin bed the resin was washed with DMF (5×~5 ml) and DCM (5×~5 ml). A further 1 volume of the acid solution was passed through the resin, taking on a pale orange colour as it did so. The resin was again washed with DMF (5×~5 ml) and DCM (5×~5 ml) and finally with diethyl ether (3×~5 ml) in readiness for the next coupling reaction.

After coupling the HOABzPS resin sample with dC, dA, T and dG amidites, using the same procedure each time and capping after the final detritylation step, the 5'-AcOG(isobu)TABzCBzABz-3'-polystyrene resin was found to weigh 2.653 g.

EXAMPLE 2

Preparation of 5'-AcOG(isobu)TABzCBzABz-3'-PDMA Resin

A poly(acrylamide) resin produced by copolymerisation of acryloyl-sarcosine methyl ester, N,N-dimethylacrylamide and bis-acryloylethylenediamine (PL-DMA resin, ex. PolymerLabs, 69 g) was treated with ethylene diamine (700 ml) in a 2L round bottomed flask which was sealed and allowed to stand at room temperature overnight. The slurry was then transferred to a sinter funnel and washed with DMF (12×700 ml). This produced DMF washings containing no trace of amine. The resin was then washed with DMF containing an increasing gradient of DCM (2.5L; 0-100% DCM) then an increasing gradient of ether in DCM (900 ml; 0-100% ether). The resin was then dried overnight in a stream of nitrogen at 40° C. The resin produced had an amino functionalisation of 973 micromoles per gram ("PDMA").

For all "dry" steps in coupling reactions (i.e. pre-coupling washes to sulfurization) the DMF used was commercial anhydrous DMF (ex Aldrich), which was dried overnight over molecular sieves in ca. 100 ml batches as required. This gave DMF with a moisture content of 10-50 ppm (Karl-Fischer), c.f. ~150 ppm as initially supplied. Discharging solutions was achieved in these steps by applying a positive pressure of N$_2$ gas to the top of the reactor via the Rotaflo tap and sucking under vacuum at the same time. The resin used initially in this series of reactions was 0.56 mmolg$^{-1}$ of 5'-HOABz-3'-PDMA resin prepared following the same procedure used for 5'-HO-ABz-3'-succinate-polystyrene in Example 1, except that PDMA was employed in place of the polystyrene. All phosphoramidites were 5'-dimethoxytrityl protected deoxyribo-3'-betacyanoethyloxy-N,N-diisopropylphosphoramidites.

The 5'-HOABz-3'-PDMA resin (1.00 g, 0.56 mmol) was charged to the jacketed solid-phase reactor, which was fitted with a septum inlet and a Rotaflo tap. Both the nitrogen inlet and outlet were fitted with in-line drying tubes filled with self-indicating P$_2$O$_5$. The resin was washed with dry DMF (4×~5 ml) and dry DCM (1×~5 ml). The amidite (1.16 g, 2.5 eq) was dried azeotropically with MeCN (2×10 ml) and dissolved in dry DCM (~5 ml). N-methylimidazole salt of saccharin (0.37 g, 2.5 eq) was charged to an oven-dried vial fitted with a septum and dissolved in dry DMF (~1.5 ml) and dry DCM (~2 ml). The amidite and saccharin salt solutions were then charged to the pre-swollen resin, in that order.

After a one hour and thirty minutes hold with gentle bubbling of the mixture with N$_2$ gas, dry methanol (~3 ml) was added. After ca. 5 minutes the solution was discharged from the reactor and the resin was washed with dry DMF (3×~5 ml). The spent reagent solution was analysed by HPLC to estimate the amount of active amidite remaining at the end of reaction.

A solution of 3-amino-[1,2,4]-dithiazole-5-thione (0.21 g, 2.5 eq) in dry pyridine (~7 ml) was charged to the resin and this was held, with gentle N$_2$ bubbling, for one hour after which the solution was discharged. The top was removed from the reactor and the resin was washed with bench DMF (5×~10 ml) and DCM (5×~10 ml) and then with Cap A solution (5:3:2 DCM:Pyridine:N-methylimidazole, 3×~10 ml). Cap A solution (5 ml) and Cap B solution (4:1 DCM:Ac$_2$O, 5 ml) were mixed and then charged to the reactor and the mixture was held for one hour.

The spent capping solution was discharged and the resin was then washed with DMF (5×~10 ml) and DCM (5×~10 ml) and finally with diethyl ether (3×~15 ml). The resin was then left overnight before detritylation.

Prior to detritylation the reactor jacket was cooled to 0° C. and the resin was washed/pre-swollen with DCM. A 5% dichloroacetic acid solution in DCM was prepared (100 ml for 1 mmol DMT expected to be attached to the resin i.e. here 60 ml). This solution (15 ml) was charged to the reactor—a deep red colouration appeared—and held for thirty seconds before being discharged. The resin was held under suction while fresh acid solution (30 ml) was passed through the bed. A last aliquot of the acid solution (15 ml) was held on the resin for one minute at which point the spent solution was discharged. The resin was then washed with DMF (5×~10 ml) and DCM (5×~10 ml). The cycle was repeated, until testing of the beads with acid after washing with DCM did not cause the appearance of red colouration. At this point the resin was washed with diethyl ether (3×~15 ml) to collapse the resin in readiness for the next coupling reaction.

After coupling the 5'-HOABz-3'-PDMA resin sample with dC, dA, T and dG amidites, using the same procedure each time and capping after the final detritylation step, the 5'-AcOG(isobu)TABzCBzABz-3'-PDMA resin was found to weigh 1.80 g.

EXAMPLE 3

10 Liter Scale Preparation of trityl-tetraethyleneglycoxystyrene

STAGE 1

Tetraethylene glycol (4188 g, 21.5 mol) was added under a nitrogen atmosphere to a 10 l vessel equipped with a mechanical stirrer and stirred at 60 rpm. Pyridine (544 g, 6.9 mol) was added to the vessel and the mixture heated to 50° C. Triphenylmethyl chloride (1000 g, 3.6 mol) was dissolved in toluene (3000 ml) under $N_2$ atmosphere and added slowly to the glycol keeping the temperature below 60° C. The temperature was held at 50° C. for 2 hours and then cooled to room temperature. 2 l of toluene were added and the mixture extracted with 6 l of deionised water, the water phase extracted with 5 l of toluene. The combined organic extracts were washed with 2×4 l of deionised water, dried over 500 g sodium sulphate and solvent removed under reduced pressure to yield 1230 g (74% based on trityl) of a pale yellow oil, 94.3% purity (by NMR).

STAGE 2

Mono(trityl)tetraethyleneglycol (1766.4 g, 3.8 mol) was added to a 10 l vessel together with 3 l tetrahydrofuran (THF) and cooled under agitation to −12° C. p-Toluenesulphonyl chloride (945 g, 5 mol) was added to the glycol/THF mixture. A solution of KOH (880 g, 15.7 mol) in deionised water (3 l) was added to the solution over 1 hour keeping the temp below −5° C. After completion of the addition the vessel was warmed to 25° C. and held for 12 hours. The phases were separated and the lower aqueous layer washed with 2×2.5 L THF, the organic layers combined and solvent removed under reduced pressure. The orange/brown oil in 7.5 l isopropyl acetate was extracted with 10 l water and then 5×2 l water, dried over magnesium sulphate (500 g) and solvent removed to give 1837 g (78.0%) of the product as a viscous orange oil, purity 95.3% (by NMR).

STAGE 3

Deoinised water (1.5 l) and THF (2.1 l) were added to a 10L vessel and agitation started at 100 rpm. The vessel was cooled down to −12° C. and potassium hydroxide (535 g, 9.5 mol) was added slowly. Acetoxystyrene (575 ml, 3.7 mol) in THF (1 l), was added to the vessel over about 30 minutes with cooling. The vessel was heated to 30° C. and held for 1 hr, then cooled to 20° C. The Stage 2 product (1800 g, 2.9 mol) in 1050 ml THF was added to reaction vessel over 15 mins, then the mixture heated at 60° C. for 40 hrs. The reaction was cooled, the phases separated and the organic layers washed with 2×2 l of 8M aqueous potassium hydroxide. The solvent was removed under reduced pressure and the residue dissolved in toluene (5 l), washed with 3×2 l deionised water, then 2×2 l 1M aqueous sodium hydroxide, and finally 2×3 l deionised water. The organic layer was dried with sodium sulphate (500 g) and solvent removed under reduced pressure to yield 1471 g (75%) of the product as an orange oil, purity 79.7% by NMR.

Synthesis of Tetraethyleneglycol-functionalised Polymer and Subsequent Deprotection Partially hydrolysed poly(vinyl alcohol) (Airvol 540, 34.9 g of 2.5 wt-% aqueous solution) and sodium chloride (31.2 g) were charged into a 2 l cylindrical baffled reactor containing deionised water (1181 ml) and equipped with a mechanical stirrer. A mixture of Stage 3 product (79.7%, 87.2 g), styrene (59.1 g), divinylbenzene (80%, 1.4 g) and lauroyl peroxide were charged to the reactor and agitated at 400 rpm. After 20 minutes the stirrer speed was reduced to 300 rpm and the reaction heated with a water bath to 80° C. over 50 minutes. After 16 h, the reaction mixture was cooled, transferred to a 50 μm filter cloth bag and washed with deionised water (5×1 l). The polymer beads were then washed with THF (4×1 l) and dichloromethane (DCM, 2×1 l) and stirred at room temperature under nitrogen in a 5 l flange flask/overhead stirrer with a mixture of dichloromethane (1800 ml), trifluoroacetic acid (128 g) and triethylsilane (51.5 g) for 4 hours. The product was then washed with dichloromethane (4×1 l) and hexane (5×1 l) before drying to constant weight in a vacuum oven, yielding 78 g of white polymer beads with a hydroxyl loading of 0.97 mmol/g.

Coupling of 5'-DMTrOABz-3'-Succinate with Tetraethyleneglycol-functionalised Polymer Tetraethyleneglycol-functionalised polymer prepared by the preceding step (0.51 g, 0.357 mmol) was charged to a 50 ml round-bottomed flask equipped with a small magnetic follower. 5'-DMTrOABz-3'-succinate (1.28 g, 4 eq) and hydroxybenzotriazole (HOBt, 0.29 g, 6 eq) were dissolved in N-methylpyrrolidinone (NMP, ca. 5 ml) and diisopropylcarbodiimide (DIC, 0.19 g, 4.2 eq) was added to this solution. Diisopropylethylamine (0.19 g, 4.1 eq) was added to this solution ca. two minutes after the DIC had been added. This whole solution was swirled then quickly added to the flask containing the resin. Glassware and equipment contaminated with DIC was detoxified in a bath of 2 M sodium hydroxide.

The flask was stoppered and the mixture was stirred slowly for ca. 70 hours. The red/brown mixture was transferred to a sinter funnel and filtered under suction and the resin was washed with NMP (3×~20 ml). Any remaining free hydroxyl groups were capped by adding a solution of acetic anhydride (0.29 g, 8 eq) and dimethylaminopyridine (DMAP, 0.02 g, 0.5 eq) in NMP (~30 ml) and holding for 1 hour, bubbling nitrogen gas up through the resin bed to provide agitation. The reagents were discharged and the resin was washed with DMF (5×10 ml), DCM (5×10 ml) and was finally collapsed with diethyl ether (3×20 ml). The resin was blown dry with a stream of nitrogen and dried in a vacuum oven at room temperature overnight. The spent reagent solution was treated with NaOH solution for detoxification.

Weight of product: 0.739 g

Preparation of 5'-HOABz-3'-succinate-tetraethyleneglycol-functionalised Polymer

5'-DMTrOABz-3'-succinate-tetraethyleneglycol-functionalised polymer prepared in the preceding step (0.739 g) was charged to a solid phase reactor comprising a jacketed sintered reactor adapted for operation under a nitrogen atmosphere fitted with a septum inlet and a Rotaflo tap. Both the nitrogen inlet and outlet were fitted with in-line drying tubes filled with self-indicating $P_2O_5$. The polymer was washed with DCM (~10 ml). The reactor jacket was cooled to 0° C. with a fluid circulator. 3% v/v dichloroacetic acid (DCA) in DCM (60 ml) was passed through the resin bed under suction. A red colour developed on the beads but did not diffuse rapidly into the solution. The beads also floated on the top of the solution. Once all of the acid solution had passed through the reactor, the resin was washed with DMF (5×~5 ml) and then DCM (5×~5 ml). Washing the resin was achieved by passing a flow of nitrogen gas up through the resin bed and adding the solvent, then replacing the nitrogen supply with a vacuum to drain the resin.

With nitrogen gas flowing up through the resin bed, 3% v/v DCA solution in DCM (15 ml) was charged to the reactor. A deep red colour developed immediately. After 1 minute the nitrogen flow was swapped for a vacuum and the acid solution was discharged. A further 30 ml of 3% acid solution was passed through the resin under suction. A third 15 ml aliquot of 3% acid solution was held with the resin for 1 minute with nitrogen bubbling before being discharged under suction. The resin was washed with DMF (5×~5 ml) and DCM (5×~5 ml).

A further "hold-flush-hold" treatment was carried out as described in the preceding paragraph and after the resin had been washed it was collapsed by washing with diethyl ether (3×~10 ml).

HPLC analysis of filtrates did not show the presence of N-benzoyl adenine, as would be expected if depurination of the A nucleoside had occurred.

Synthesis of GTACA Oligonucleotide Phosphorothioate

This was achieved using phosphoramidite chemistry using the following coupling and detritylation conditions. Conventional 5'-dimethoxytrityldeoxyribonucleoside-3'-betacyanoethyloxy-N,N-diisopropylphosphoramidites were employed.

Coupling

For all "dry" steps in coupling reactions (i.e. from pre-coupling washes up to and including sulfurization) the DMF used was commercial anhydrous DMF (ex Aldrich), which was dried overnight over 4 Å molecular sieves in ca. 100 ml batches as required. This gave DMF with a moisture content of 5-50 ppm (Karl-Fischer), c.f. ~150 ppm as initially supplied. Discharging of solutions was achieved in these steps by applying a positive pressure of $N_2$ gas to the top of the reactor via the Rotaflo tap and applying suction from below the sinter. The support used initially in this series of reactions was 5'-HOABz-3'-succinate-tetraethyleneglycol-functionalised polymer prepared by the method above.

Details are given for the first coupling and detritylation in the series (dCbz amidite+5'-HOABz-3'-succinate-tetraethyleneglycol-functionalised polymer). Subsequent couplings and detritylations were executed in an identical manner using the same number of equivalents of the corresponding phosphoramidite reagent (dAbz, dT and dGibu amidites).

5'-HOABz-3'-succinate-tetraethyleneglycol-functionalised polymer (0.320 mmol) was charged to the solid-phase reactor, which was fitted with a septum inlet and a Rotaflo tap and adapted for operation under a nitrogen atmosphere. Both the nitrogen inlet and outlet were fitted with in-line drying tubes filled with self-indicating $P_2O_5$. The resin was washed with dry DMF (3×~5 ml) and dry DCM (2×~5 ml). The amidite (0.67 g, 0.8 mmol, 2.5 eq) was dried azeotropically with MeCN (2×10 ml) and dissolved in dry DCM (~3 ml). Saccharin methyl imidazole salt, prepared by the methods of International Patent Application W003/004512 (SMI, 0.21 g, 0.8 mmol, 2.5 eq) was charged to an oven-dried vial fitted with a septum and dissolved in dry DMF (~0.5 ml) and dry DCM (-2.5ml). The amidite and SMI solutions were then charged to the pre-swollen resin, in that order, via the septum inlet.

After a two hour hold with gentle bubbling of the mixture with $N_2$ gas, dry methanol (~2 ml) was added. After ca. 5 minutes the solution was discharged from the reactor and the resin was washed with dry DMF (3×~5 ml) and dry pyridine (2×~5 ml). The spent reagent solution was analysed by HPLC to estimate the amount of active amidite remaining at the end of the reaction.

A solution of xanthane hydride (0.12 g, 0.8 mmol, 2.5 eq) in dry pyridine (~4 ml) was charged to the resin and this was held, with gentle $N_2$ bubbling, for one hour after which the solution was discharged. The top was removed from the reactor and the resin was washed with bench DMF (5×~5 ml) and DCM (5×~5 ml) and then with Cap A solution (5:3:2 MeCN:Pyridine:N-methylimidazole, 2×~5 ml). Cap A solution (2.5 ml) and Cap B solution (4:1 MeCN:$Ac_2O$, 2.5 ml) were then charged to the reactor and the mixture was held for one hour.

The spent capping solution was discharged and the resin was then washed with DMF (5×~5 ml) and DCM (5×~5 ml) and finally with diethyl ether (3×~5 ml). The resin was then left overnight before detritylation.

Detritylation

Prior to detritylation the reactor jacket was cooled to 0° C. and the resin was washed/pre-swollen with DCM. 3% (v/v) DCA in DCM ("acid solution") was used to detritylate the resin. For each detritylation cycle, the volume of acid solution used was based on 167 ml per mmol of DMT assumed to be attached to the resin.

Acid solution (12 ml) was held with the resin for 1 minute with agitation by nitrogen gas from below the sinter. The bright red solution was discharged by suction and a further 25 ml of acid solution was passed through the resin bed. A third 12 ml aliquot of acid solution was held with the resin for 1 minute before being discharged. The resin was washed with DMF (5×~5 ml) and with DCM (5×~5 ml).

This cycle of acid treatment/washing was repeated once more. After the final DCM wash the resin was collapsed by washing with diethyl ether (3×~5 ml).

The average coupling yield over the 4 coupling steps was calculated by trityl analysis as 97.5%.

The invention claimed is:

1. A process for the synthesis of an oligonucleotide in which an oligonucleotide is assembled on a swellable solid support using the phosphoramidite approach in the presence of a solvent and an activator, wherein, the solvent and swellable support are selected such that a swell ratio of from 5 to 20 is achieved, swell ratio being calculated according to the formula:

$$\text{Swell Ratio} = \frac{Vol_{final} - Vol_{initial}}{Vol_{initial}}$$

wherein $Vol_{final}$ is the final volume occupied by the swellable support after full swelling; and $Vol_{initial}$ is the initial dry bed volume of the swellable support, the activator being selected from the group consisting of i) compounds having the chemical formula (1):

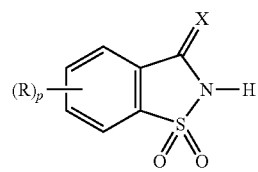

wherein p is 0 or an integer from 1 to 4; X is O or S; and R for each occurrence is a substituent selected from the group consisting of halo groups, aliphatic groups, —$NR^1R^2$, —$OR^3$, —$OC(O)R^3$, —$C(O)OR^3$, cyano, aryl groups, heterocyclyl groups, —CHO, —$COR^3$, —$NHCOR^3$, aralkyl groups, and —$SR^{13}$, wherein $R^{11}$ and $R^{12}$ are each, independently, —H, an aliphatic group, an aryl group, an aralkyl group; or together with the nitrogen to which they are attached form a 5 or 6-membered heterocyclic ring; and $R^{13}$ is an aliphatic group, an aryl group, or an aralkyl group; or two adjacent R groups taken together with the carbon atoms to which the are attached form a six membered saturated or unsaturated ring; and ii) salts formed between a compound of chemical formula (1) and an organic base.

2. A process according to claim 1, wherein the activator is the N-methylimidazobe, pyridine or 3-methylpyridine salt of a compound of formula (1) wherein X is O and p is 0.

3. A process according to claim 1, wherein the swellable support comprises functionalised polystyrene, partially hydrolysed polyvinylacetate or poly(acrylamide).

4. A process according to claim 1, wherein the process comprises coupling a nucleoside phosphoramidite with a nucleoside or oligonucleotide comprising a free hydroxy group.

5. A process according to claim 4, wherein the nucleoside phosphoramidite is a deoxyribonucleside-3'-phosphoramidite or ribonucleside-3'-phosphoramidite.

6. A process according to claim 4, wherein the nucleoside or oligonucleotide comprising a free hydroxy group comprises a free 5'-hydroxy group.

7. A process according to claim 4, wherein the nucleoside or oligonucleotide comprising a free hydroxy group is attached to the solid support by a cleavable linker.

8. A process according to claim 1, wherein the solvent is dimethylformamide, N-methylpyrrolidinone, dichloromethane, tetrahydrofuran or pyridine.

9. A process according to claim 1, wherein the assembled oligonucleotide is cleaved from the solid support.

10. A process for the synthesis of an oligonucleotide which comprises coupling a nucleoside phosphoramidite with a nucleoside or oligonucleotide comprising a free hydroxy group in the presence of an activator, wherein:
  a) the nucleoside or oligonucleotide comprising a free hydroxy group is attached to a swellable solid support by a cleavable linker, said swellable support being selected from the group consisting of functionalized polystyrene, partially hydrolyzed polyvinylacetate and poly(acrylamide);
  b) said activator is a salt formed between an organic base and a compound having the chemical formula:

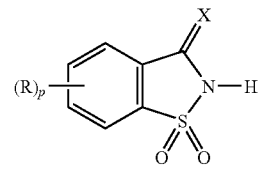

wherein p is 0 or an integer from 1 to 4;
  R for each occurrence is a substituent selected from the group consisting of halo groups, aliphatic groups, —NR1R2, —OR3, —OC(O)R3, —C(O)OR3, cyano, aryl groups, heterocyclyl groups, —CHO, —COR3, —NHCOR3, aralkyl groups, and —SR13, wherein R11 and R12 are each, independently, —H, an aliphatic group, an aryl group, an aralkyl group; or together with the nitrogen to which they are attached form a 5 or 6-membered heterocyclic ring; and R13 is an aliphatic group, an aryl group, or an aralkyl group; or two adjacent R groups taken together with the carbon atoms to which they are attached form a six membered saturated or unsaturated ring; and X is O or S;
  the process employing a solvent which swells the solid support selected from the group consisting of dimethylformamide, N-methylpyrrolidinone, dichloromethane, tetrahydrofuran and pyridine.

11. A process according to claim 10, wherein the activator is the N-methylimidazole, pyridine or 3-methylpyridine salt of a compound of formula (1) wherein X is O and p is 0.

* * * * *

UNITED STATES PATENT AND TRADEMARK OFFICE
CERTIFICATE OF CORRECTION

PATENT NO. : 7,635,772 B2  Page 1 of 1
APPLICATION NO. : 10/539625
DATED : December 22, 2009
INVENTOR(S) : Paul McCormac It is certified that error appears in the above-identified patent and that said Letters Patent is hereby corrected as shown below:

In the claims, column 14, claim 1, line 62, "$SR^{13}$" should read --$SR^3$--, "$R^{11}$" should read --$R^1$--, and "$R^{12}$" should read --$R^2$--.

In the claims, column 14, claim 1, line 65, "$R^{13}$" should read --$R^3$--.

In the claims, column 16, claim 10, line 18, "SR13" should read --$SR^3$--.

In the claims, column 16, claim 10, line 19, "R11 and R12" should read --$R^1$ and $R^2$--.

In the claims, column 16, claim 10, line 22, "R13" should read --$R^3$--.

Signed and Sealed this

Eleventh Day of May, 2010

David J. Kappos
*Director of the United States Patent and Trademark Office*